United States Patent [19]
Forssmann et al.

[11] Patent Number: 5,449,751
[45] Date of Patent: Sep. 12, 1995

[54] CARDIODILATIN FRAGMENT, PROCESS FOR PREPARING SAME AND USE THEREOF

[75] Inventors: Wolf-Georg Forssmann, Im Langgewann 93, D-6900 Heidelberg 1; Jeanette M. Alt, Burgwedel; Gerhard Becker, Neckargemund; Franz Herbst, Leimen, all of Germany

[73] Assignees: Pharma Bissendorf Peptide GmbH, Hanover; Wolf-Georg Forssmann, Heidelberg, both of Germany; a part interest

[21] Appl. No.: 185,240

[22] Filed: Jan. 24, 1994

Related U.S. Application Data

[63] Continuation of Ser. No. 994,084, Dec. 16, 1992, abandoned, which is a continuation of Ser. No. 795,248, Nov. 18, 1991, abandoned, which is a continuation of Ser. No. 401,401, Sep. 1, 1989, abandoned, which is a continuation-in-part of Ser. No. 100,144, Aug. 28, 1987, abandoned.

[30] Foreign Application Priority Data

Mar. 2, 1987 [DE] Germany ......................... 37 06 731.1
May 22, 1987 [DE] Germany ......................... 37 17 329.4
Dec. 9, 1987 [DE] Germany ......................... 37 41 641.3

[51] Int. Cl.$^6$ ...................... C07K 14/00; A61K 38/16
[52] U.S. Cl. .................................................. 530/324
[58] Field of Search ........................... 530/324; 514/12

[56] References Cited

U.S. PATENT DOCUMENTS 4,643,989 2/1987 Baird ....................... 514/12
4,751,284 6/1988 Forssmann ................. 530/329
4,782,044 11/1988 Forssmann ................. 514/12

FOREIGN PATENT DOCUMENTS

WO/85/048-
70 11/1985 WIPO ................. 530/324

OTHER PUBLICATIONS

Palluk, R., et al., *Life Sciences,* 36:1415–1425, 1985.
Nahao, K., et al., *Horumon To Rinsho,* 33(4): 365–370, 1985.
Kangawa, Kog et al., *Biochemical & Biophysical Research Communications,* 121(2): 585–591, 1984.
Seidah, N., et al., *Proc. Natl. Acad. Sci.,* 81: 2640–2644, May 1984.
Flynn, T., et al., *Biochemistry,* 232: 313–321, 1985.
Stewart et al., Solid Phase Peptide Synthesis, 2nd Ed, Pierce Chemical Co., 1984.
Oikawa, S., et al., *Nature,* (309: 724–726, Jun. 1984.
Seidman, C., et al., *Science,* 226: 1206–1209, 1984.
Seidah et al. Proc. Natl. Acad. Sci., 81: 2640–2644, May 1984.

*Primary Examiner*—Jill Warden
*Assistant Examiner*—Carol A. Salata
*Attorney, Agent, or Firm*—Jacobson, Price, Holman & Stern

[57] ABSTRACT

Described is a peptide fragment which comprises the amino acid sequence 95–126 of ANF/CDD 1–126 (gamma-hANaP) and is formed in the kidney. The fragment urodilatin (ANF/CDD 95–126) has the following amino acid sequence:

$$R^1\text{-Cys-Phe-Gly-Gly-Arg-Met-}$$
$$\diagdown\text{S}$$
$$\diagdown\text{S}$$
$$\text{Asp-Arg-Ile-gly}=\text{Ala-Gln-Ser-Gly-Leu-Gly-Cys-}R^2,$$

wherein $R^1$ and $R^2$ each represent further peptide fragments of ANF/CDD 1–126 (gamma-hANaP). In the amino acid sequence $R^1$ is Thr-Alo-Pro-Arg-Ser-Leu-Arg-Arg-Ser-Ser and $R^2$ is Asn-Ser-Phe-Arg-Tyr. Further described are processes for the preparation and/or recovery of the new peptide fragment and a medicament containing urodilatin (ANF/CDD 95–126) as well as medical indications of the medicament.

4 Claims, 12 Drawing Sheets

CARDIODILATIN FRAGMENT, PROCESS FOR PREPARING SAME AND USE THEREOF

This application is a continuation of U.S. application Ser. No. 07/994,084 filed Dec. 16, 1992 now abandoned; which is a continuation of Ser. No. 07/795,248 filed Nov. 18, 1991 now abandoned; which is a continuation of Ser. No. 07/401,401 filed Sep. 1, 1989, now abandoned, which is a continuation in part of application Ser. No. 07/100,144, filed Aug. 28, 1987, now abandoned.

The invention relates to a new cardiodilatin fragment, a process for preparing same and a medicament containing said fragment.

Biologically active peptides such as, more particularly, hormones are produced in low amounts in various endocrine glands and are transported via the blood to the target organs. There they control quite a number of physiological and metabolic activities. As a rule, inactive forms of the respective peptides are synthesized in the respective endocrine gland and are converted into their active forms under the action of proteases. Only in such active forms they exert the desired effect on the target organ.

In the last years atrial extracts from rat atria have been thoroughly investigated. As a result, a number of different peptides has been isolated which display stronger or lesser sodiuretic and diuretic effects and which additionally are capable of relaxing the smooth muscles of vessels. The nomenclature of these peptides so far was rather confusing (atrial sodiuretic factor, auriculin A, cardionatrin, auriculin B, atriopeptin I, II and III, gamma- and alpha-atrial sodiuretic factor). It is to be assumed that this variety of terms in part was caused by preparative artifacts, and that, on the other hand, different peptides were prepared from a common precursor. A common precursor of the human peptides as well as of the peptides of rats could be prepared from cloned cDNA, which had been prepared from atrial mRNA. The human prepropeptide has 151 amino acids. the first 25 amino acids of this peptide correspond to the prepeptide portion which is designated as signal peptide and controls processing along the ribosomal synthesis and the subsequent secretion. Thereafter a peptide comprising 126 amino acids, the ANF/CDD 1-126 (gamma-hANaP), is released which has a molecular weight of 13,500 and in this form has also been identified in human atria.

An essential biologically active peptide corresponds to the last 28 amino acids at the C-terminal end of ANF/CDD 1-126 (gamma-hANaP). This peptide has been designated as ANF/CDD 99-126 (alpha-human atrial sodiuretic peptide, alpha-hANaP). The amino acid sequence has been elucidated and published by Kangawa, K. and Matsuo, cf. Biochem. Biophys, Res. Commun. 118, 131-139 (1984).

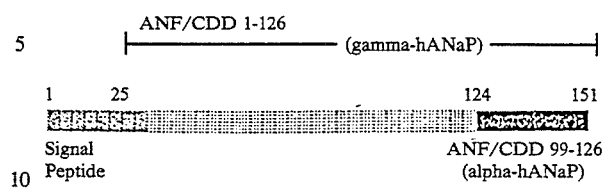

The positions 1-25 of the amino acid sequence are considered as the signal peptide, whereas the positions 25-151 represent the gamma-hANaP, which inter alia in the region of the C-terminal end (positions 124-151) is identical with the alpha-hANaP (Oikawa, S. et al., "Nature" 309 (1984), 724-726; Nakayama, K. et al., "Nature" 310 (1984), 699-701). However, the numbering as used hereinbelow will leave the signal peptide out of consideration. Thus, there is valid for gamma-hANaP an amino acid sequence of positions 1-126, and for Alpha-hANaP an amino acid sequence of positions 99-126 (ANF/CDD 99-126).

This peptide hormone which is also known under the designation of cardiodilatin is of great clinical and therapeutical importance because of its influence on renal diuresis of the inotropy of the cardiac muscle and on the smooth musculature of the vessels as well as the perspiration. Some fragments of this peptide hormone exhibit biological activity, in part in an attenuated form. ANF/CDD 99-126 is an active fragment of cardiodilatins which circulates in the blood. It has the following amino acid sequence:

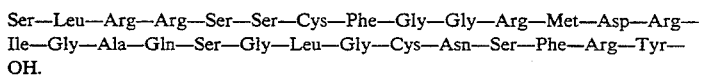

The ANF/CDD 99-126 may be obtained from atrium extracts only in infinitely small amounts.

It is the object of the present invention to find further biologically active fragments of cardiodilatin and further to create processes for the synthetic preparation of this biologically active cardiodilatin fragment.

Said object is attained by the cardiodilatin fragment urodilatin (ANF/CDD 95-126) which has the amino acid sequence

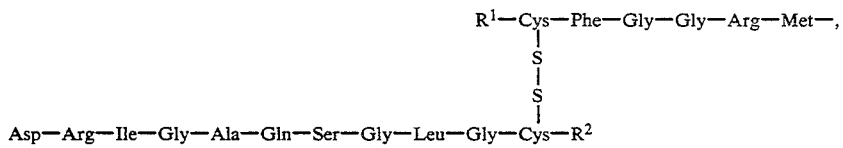

wherein $R^1$ and $R^2$ each represent further peptide fragments of ANF/CDD 1-126 (gamma-hANaP) and, more particularly $R^1$ is Thr-Ala-Pro-Arg-Ser-Leu-Arg-Arg-Ser-Ser and $R^2$ is Asn-Ser-Phe-Arg-Tyr.

Surprisingly it was found that human urine contains a so far unknown biologically active form of cardiodilatin-urodilatin (ANF/CDD 95-126). Animal tests with rats and dogs showed that urodilatin (ANF/CDD 95-126), although it displays an action corresponding to that of ANF/CDD 99-126, has a clearly stronger diuretic effect. This biologically active material is eluting in certain steps of its isolation in a manner significantly different from ANF/CDD 99-126 in the chromatographic system used for the isolation of cardiodilatin fragments.

The effect of ANF-(99–126) and urodilatin on urine flow and fractional sodium excretion in normal rats was examined in the following experiment.

The experiments were performed with 2 doses (1.0 and 2.0 μg/kg b.w.) of either ANF-(99–126) or urodilatin.

The experiments were performed on Pentobarbital anaesthetized female Sprague-Dawley rats weighing 280±6 g. All animals were maintained on tap water and a standard pellet diet. For measurements of mean arterial pressure one carotid artery was catheterized.

After 3 hr equilibration period following surgery, all animals had similar basal urine outputs, had received saline replacement for urine for the same length of time and had similar mean arterial pressures. Injections of either ANF-(99–126) or urodilatin at doses of 1.0 and 2.0 μg/kg were given as an intra-arterial bolus over 1 min. in random order over a period of 5 hours, each injection separated by at least 60 min. Throughout the experiment urine losses were replaced with saline to maintain hematocrit levels.

Results (mean ± SEM) of effects of ANF-(99–126) or urodilatin on fractional sodium excretion and urine volume and time course are shown in the added figures. The numbers above the bars represent the number of experiments.

The administration of hANF-(99–126) and Urodilatin caused a prompt (the effects are visible within 5 min.) and potent diuretic activity in normal rats. The sodium excretion seems to follow a similar trend as the urine flow. Surprisingly, the effect of Urodilatin seems to be more potent compared with ANF-(99–126).

The results of the above experiment are exemplified in FIGS. 7–10.

The effect of hANF-(99–126) and urodilatin on urine volume and blood pressure in conscious, chronically instrumented dogs was examined in the following experiment.

Female Beagle-dogs, who were kept under standardized conditions (e.g. on a sodium diet of 2.5 mMol sodium/kg body weight) were used. For experimental study the dogs had arterial and venous catheters. After a control period of 1 hour, in which every 20 minutes excretory values were determined, a dosage of 30 μg ANF-(99–126) or urodilatin was injected as a bolus. The weight of one dog was approximately 15 kg. The study was continued over a period of 2 hr. Urine volume was measured and blood pressure (mean arterial pressure) was monitored.

Results (mean value ± SEM) of time course and effects of ANF-(99–126) and urodilatin induced changes are shown in FIGS. 11 and 12. The administration of-ANF-(99–126) and urodilatin caused an increase in diuresis within 5 min. Surprisingly, the effect of urodilatin seems to be more prominent in comparison to ANF-(99–126). The mean arterial pressure remained nearly unchanged after bolus injection of ANF-(99–126), whereas urodilatin seems to have a more potent effect on blood pressure in this species.

It was found that urodilatin (ANF/CDD 95-126) originates from precursor proteins formed in the kidneys by post-translator processing.

|———ANF/CDD 1-126 (gamma-hANaP)———|

```
1    25                                    120      151
▓▓▓▓▓▓▓▓▓▓░░░░░░░░░░░░░░░░░░░░░░░░░░░░░░░░▓▓▓▓▓▓▓▓
Signal                                     Urodilatin
Peptide                                    (ANF/CDD 95-126)
```

Another unexpected result is evident from receptor binding studies carried out for ANF-(99–126) and urodilatin.

In this study the binding properties of platelet ANF-(99–126) and urodilatin receptors were investigated. Additionally, receptor sites in bovine cortico-adrenal cells were measured. Human platelets and bovine cortico-adrenal cells are easily accessible cells with ANF and urodilatin receptors.

Fragments of fresh bovine adrenals were homogenized in buffer solution containing 20 mM $NaHCO_3$ and 1 mM EDTA. The final pellet was resuspended in buffer, containing 50 mM Tris-Cl pH 7.4, 250 mM sucrose and 0.1 mM EDTA.

Platelets were isolated by Percoll gradient centrifugation and counted.

The platelet suspension was mixed with $^{125}J$-ANF-(99–126) and with increasing concentrations of unlabeled rat ANF. Identically, $^{125}J$-ANF and unlabeled ANF-(99–126) were incubated at 25° C. in buffer containing cortico-adrenal membrane cells. Membrane bound $^{125}J$-ANF was separated by filtration on glass fiber filters, followed by washing with buffer. $^{125}J$-ANF, retained on filter, was then measured in a gamma counter.

The results were as follows. Binding capacities were identical for ANF-(99–126) and urodilatin receptors in platelets (55 pM vs. 55 pM). ANF receptors on platelets most likely are not coupled to particulate guanylate cyclase and may represent the R2 or C receptor, that only might constitute the function of a capacity receptor that buffers free ANF.

Surprisingly, a significant difference has been observed in binding properties of the ANF-(99–126) and urodilatin receptors of cortico adrenal membrane cells (78pM vs. 35 pM). ANF receptors on cortico adrenal cells most likely are coupled to activate particulate guanylate cyclase. this receptor type, e.g., is supposed to be responsible for vasorelaxation.

The present data further underline a difference in potency between ANF-(99–126) and urodilatin.

The following data also indicate that alpha-hANaP is rapidly inactivated by a membrane preparation from dog kidney cortex. However, in contrast urodilatin being released from kidney is not destroyed by proteolysis using the identical membrane preparation. This data was presented in a paper to FEBS letters for publication by Michael Gagelmann, Dieter Hock and Wolf-Georg Forssmann of the Institute of Anatomy and Cell Biology, University of Heidelberg, Im Neuenheimer Feld 307, D-6900 Heidelberg, FRG entitled "Urodilatin (CDD/ANP-95-126) is not Biologically Inactivated by Specific Cleavage of a Peptidase from Dog Kidney Cortex Membranes in Contrast to Atrial Natriuretic Peptide/Cardiodilatin (alpha hANP/CDD-99–126)" which is incorporated herein by reference.

It was demonstrated that atrial natriuretic peptide (CDD/ANP-99-126) is rapidly inactivated by a membrane preparation from dog kidney cortex. Inactivation occurs by cleavage of the ring structure in position between Cys-105 and Phe-106. A unique proteolytic product separated by HPLC on a reverse phase column appears as a single peak which eluates prior the intact peptide. In contrast CDD/ANP-95-126 (urodilatin) that is released from the kidney is not destroyed by proteolysis using the identical membrane preparation.

In further support of the differences between alpha-hANaP and urodilatin, the folowing data was presented at the 61st Scientific Sessions of the American Heart Association, Nov. 14–17, 1988 in Washington D.C. Hemodynamic, hormonal and renal effects of a new 32 amino acid residue of ANP-1-126 was investigated. Urodilatin (ANP-95-126), most likely originated from renal tubules, in healthy dogs and dogs with CHF (rapid right ventricular pacing 260/min.). In this setting, iv alpha-AN; (99–126) over a whole dose-response (0.01 to 0.6 µg/kg/min.) had no renal effects in CHF. In control dogs urodilatin in equimolar concentrations sign. (p<0.001) reduced right atrial pressure (RAP), SV, CO. MAP and increased HR, PAP and PVR were unchanged. In contrast to alpha-ANP, no suppression of renin and aldosterone was observed. Urine flow and sodium excretion increased 2.4-fold (p<0.001). In CHF, unlike alpha-ANP, urodilatin stimulated urine flow 2.6-fold and sodium excretion 3-fold (p<0.001). Under both conditions the dose-response curve was markedly shifted to the left, plasma cGMP was identically stimulated. In CHF urodilatin decreased RAP (p<0.002) and PAP (p<0.001): CO, MAP, PVR, renin and aldosterone were unchanged. Urodilatin has similar hemodynamic effects as alpha-ANP but its renal activity are much more potent, promising a new effective therapeutic approach in CHF.

The positions 1–25 of the amino acid sequence of the prepropeptide are considered as the signal peptide, whereas the positions 25–151 represent the ANF/CDD 1–126 (gamma-hANaP) (Oikawa, S. et al., "Nature" 309 (1984), 724–726; Nakayama, K. et al., "Nature" 310 (1984), 699–701), which in the region of the C-terminal end (positions 120–151) is identical with the urodilatin (ANF/CDD 95-126). However, the numbering as used hereinbelow will leave the signal peptide out of consideration. Thus, there is valid for ANF/CDD 1-126 (gamma-hANaP) an amino acid sequence of positions 1–126, and for urodilatin (ANF/CDD 95-126) an amino acid sequence of positions 95-126.

This new cardiodilatin fragment which has a surprising biological activity and is distinguished from ANF/CDD 99-126, was isolated from human urine in an amount sufficient for elucidating its structure and was obtained in a particularly pure state by means of HPLC techniques, so that as a singularly molecule its structure could be elucidated by an amino acid sequence analysis. The amino acid sequence of this fragment was: Thr-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr.

In vivo- and in vitro investigations on the activities of urodilatin (ANF/CDD 95-126) show that this substance has a marked relaxant effect on the smooth musculature. In vitro investigations of the *Arteria renalis* of rabbits, of the *Aorta abdominalis* of rabbits or rats of the *Arteria pulmonalis* of rabbits in the organ bath, which have been contracted by adrenalin pretreatment, also show a relaxant effect of the urodilatin (ANF/CDD 95-126). Most clearly evident is this relaxation in muscle stripes from *Arteria renalis*. There the relaxation is already detectable at doses of about 1.0 to 10.00 mg per 10 ml in the organ bath. Urodilatin (ANF/CDD 95-126) acts vasodilative as well as diuretic and sodiuretic.

While ANF/CDD 99-126 may be isolated from material obtained in hemodialysis or hemofiltration, respectively, urodilatin may be isolated from human urine. For a recovery of urodilatin (ANF/CDD 95-126) urine, if appropriate after acidification, is first contacted with alginic acid. The cardiodilatin fragments will be adsorbed on the alginic acid. The work-up and isolation of the cardiodilatin fragments by detaching same from the alginic acid and chromatographic purification are carried out as already described in the DE-OS 33 46 953 for the total molecule ANF/CDD (gamma-hANaP).

For effecting still further purification of the desired biologically active cardiodilatin fragment, the fraction containing the biologically active molecule may be subjected to a second separation by HPLC using a reversed-phase chromatography silicagel. In this second chromatography step it is preferred to use a mixture comprising water, methanol and trifluoroacetic acid with a continuous gradient as eluant.

This new cardiodilatin fragment urodilatin (ANF/CDD 95-126) may also be synthesized in a per se known manner, e.g. by Merrifield synthesis using BOC amino acids. A preparation is also possible by way of a classical fragment synthesis in solution.

Another subject matter of the invention is a process for the preparation of the cardiodilatin fragment urodilatin (ANF/CDD 95-126) having the amino acid sequence:

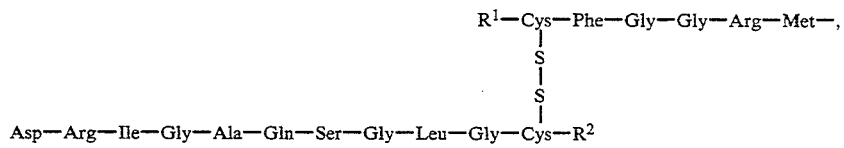

wherein $R^1$ and $R^2$ each represent further peptide fragments of ANF/CDD 1-126 (gamma-hANaP) and, more particularly $R^1$ is Thr-Ala-Pro-Arg-Ser-Leu-Arg-Arg-Ser-Ser and $R^2$ is Asn-Ser-Phe-Arg-Tyr, by stepwise synthesis on a solid phase using amino acid protected with conventional protective groups.

As the protective groups there are preferably used tert-butyloxycarbonyl, fluorenylmethoxycarbonyl or 3,5-dimethoxy-phenyl-w,w-propyloxycarbonyl groups.

In a further embodiment of the process according to the invention, ANF/CDD 99-126 is directly reacted with the N-terminally extending tetrapeptide Thr-Ala-Pro-Arg-OH. Since the peptide ANF/CDD 99-126 does not contain pendant groups having free amino functions, this synthesis may be carried out relatively free from problems. The tetrapeptide Thr-Ala-Pro-Arg is previously synthesized in a per se known manner and reacted, if appropriate in its protected form, with free ANF/CDD 99–126 after activation of its carboxyl functions.

Another embodiment of the process according to the invention for the preparation of the cardiodilatin fragment urodilatin (ANF/CDD 95–126) is characterized in that ANF/CDD 99–126, which has been immobilized on a solid phase, is reacted with the tetrapeptide Thr-Ala-Pro-Arg which, if appropriate, contains protective group(s), the resulting peptide is detached from the carrier, subjected to cyclization upon removal of the protective group(s) and worked up and purified in a per se known manner.

The tetrapeptide may have been protected by conventional protective groups. Preferably used tetrapeptides are Fmoc-Thr(But)-Ala-Pro-Arg(Mtr) or Ddz-Thr(But)-Ala-Pro-Arg(Mtr). the pendant group of Arg in the tetrapeptide may also be present protected in the salt form as bromide or perchlorate.

As an activating agent there is preferred to be used carbonyldiimidazol with 2 equivalents of 1-hydroxybenzotriazole.

A further subject matter of the invention is a process for the preparation of the cardiodilatin fragment urodilatin (ANF/CDD 95–126) which process is characterized in that the peptide ANF/CDD 99–126 is dissolved in a solvent, the tetrapeptide Thr-Ala-Pro-Arg, provided with protective group(s) if appropriate, is added together with an activating agent, and the resulting product is subjected to chromatography after removal of the protective groups and further purified in a per se known manner.

The urodilatin (ANF/CDD 95–126) having been completely synthetically prepared by means of the solid phase synthesis method according to Merrifield (R. B., "Solid Phase Peptide Synthesis I, The Synthesis of a Tetrapeptide", J. Am. Chem. Soc. 85 2149–2156, (1963)) using BOC amino acids is obtained as a very pure substance (purity more than 98%) and in a very active form.

The synthesis of urodilatin (ANF/CDD 95–126) may be carried out by analogy of the solid phase synthesis method of Merrifield (1963) by means of benzhydrylamine as a supporting polymer in an automatic peptide synthesizer. The crude preparation is pre-purified over Sephadex-G 25 (F) and subsequently purified by means of a semi-preparative high pressure liquid chromatography (HPLC). Thus, the fully synthetic replicate of the last C-terminal amino acids (95 to 126) of ANF/CDD 1–126 (gamma-hANaP) is formed. The product is obtained in a freeze-dried form as a white and flocculent low-density powder. the purity of said product is at least 98%. It may be drawn off in amounts of from 10 to 500 μg and be dissolved prior to use in physiological saline (0.9% of NaCl). For example, the substance is drawn off in amounts of 50 μg as a lyophilized powder without auxiliary materials in 2 ml glass vials. 1 ml of physiological saline (0.9% of NaCl) was used for dissolution. These solutions may be perfectly injected or infused. Basically there is also the possibility to prepare and store the peptide in a physiological saline or any other isotonic physiologically compatible solution. Optionally a physiologically compatible disinfectant and/or stabilizer will be added to these solutions.

In order to determine the respective fractions containing the desired biologically active cardiodilatin fragment in chromatographic separations, per se known methods for detecting the biological activity are employed. For the detection of urodilatin (ANF/CDD 95–126) or of ANF/CDD 99–126 in one fraction, there is suitable the relaxing effect of the compounds on the smooth musculature. In this assay, it is preferred to use the *Arteria renalis* of rabbits, the *Aorta abdominalis* of rabbit or rat or the *Arteria pulmonalis* of rabbits in the organ bath, where the stripes of vessel muscles contracted upon a norepinephrine pretreatment show a significant relaxation after the addition of the active cardiodilatin fragment. This reaction is best recognizable in muscle stripes from *Arteria renalis*, with which the relaxation is detectable already at doses of about from 1.0 to 10.00 mg per 10 ml in the organ bath.

It appears that the disulfide bridge is contained between the amino acids Cys 105 and Cys 121 is essential for the biological action.

These biological actions show that the peptide hormone cardiodilatin, and surprisingly the fragment urodilatin (ANF/CDD 95–126) as well, have a great clinical, diagnostic and therapeutic importance. More specifically, the cardiodilatin fragment urodilatin (ANF/CDD 95–126) is suitable for the following fields of application: differentiated vasodilation of certain vessel beds, diagnostics and therapy of hypertonia, application as a substitution for patients, which have been implanted with artificial hearts, synchronous regulation of blood volume and electrolytes of the blood, skin diseases, and more particularly those including perspiration disorders, cardiovascular shock, renal and adrenal cortical disorders, diseases of the gastro-intestinal tract, and more particularly motility disorders and obstipation, therapy of brain edemae and of glaucoma, therapy of spastic coronaropathies such as angina pectoris, for the treatment of acute renal insufficiency, nephrotic and nephritic syndrome, terminal renal insufficiency, acute coronary insufficiency, ascites, generalized edemae, lung edema, brain edema, primary and secondary lymph edemae, hydrothorax, glaucoma, vena cava stenosis, hypoproteinemia, hearing impairment, essential and renal hypertonia, malignant hypertonia, EPH gestosis such as hypertonia of pregnancy, nephrosis of pregnancy, cerebral sodium storage syndrome, vessel spasms such as Morbus Raynaud, angina abdominalis, coronary spasms, coronary heart disease, vasomotor headache, headache upon hypertonia, Bing-Horton syndrome migraine, blood circulation disorders in the vertebralis-basilaris flow path region, disorders of the renin-angiotensin system, primary and secondary hyperaldosteronism, renin-secernent tumors, pheochromocytoma, Bartter's syndrome, Schwartz-Bartter's syndrome, pancreas insufficiency, primary sweat gland insufficiency such as anhidrosis, miction and defecation disorders, dysregulation of the anterior lobe of the pituitary gland, cardiovascular side-effects in the therapy of psych(iatr)ic diseases and agitation with catechol increase, for the supporting treatment upon heart transplantations, "PEEP-respiration" (an artificial respiration with positive and expiratory pressure) as well as by-pass operations and for the treatment of complications after implantation of an artificial heart. Urodilatin (ANF/CDD 95–126) may also be employed as a diuretic for the treatment of multiple diseases such as gout combined with hypertonia/heart insufficiency, as well as diabetes with hypertonia/heart insufficiency, or as a diuretic in combination with cephalosporins, aminoglycosides or anticoagulants. Urodilatin (ANF/CDD 95–126) is further suitable for the prophylaxis of an acute renal failure after kidney transplantations and treatment with nephrotoxic substances such as cyclosporin, cisplatin and ifosfamid and for the prophylaxis of an acute kidney failure which may occur postoperative or after hypertonic crisis as well as after dosis of contrast media for patients suffering from limited functions of the kidney. The agent according to the invention is also usable as a diagnostic for differential diagnostics of endothelial changes.

Therefore, subject matter of the invention is also medicaments containing the new cardiodilatin fragment urodilatin (ANF/CDD 95-126) for use in the diagnosis and therapy methods as set forth above. The medicaments may be present in the conventional application forms for intravenous, oral or parenteral administrations such as, e.g., as tablets, suppositories, dragées, solutions, sprays or preparations for inhalation etc., as well as micro-encapsulation, if desired in combination with conventional pharmacological excipients and/or diluents. The medicament according to the invention can also be formulated as slow-release-form. Preferably the amount of urodilatin (ANF/CDD 95-126) is from 50 µg to 50 µg per unit dose.

Furthermore, according to the invention there is provided a method for the specific determination of cardiodilatin which is based on the principle of immuno-assay and employs an antibody directed against urodilatin (ANF/CDD 95-126). Surprisingly it has been determined that by using antibodies directed against urodilatin (ANF/CDD 95-126) cardiodilatin can be highly specifically and very accurately detected in body liquids. Said method for the specific determination of cardiodilatin can be used for the diagnosis of neurological diseases by specifically determining cardiodilatin or its fragments in the liquor cerebrospinalis.

The use of the medicament according to the invention which contains, as the active substance, urodilatin (ANF/CDD 95-125), due to the beneficial spectrum of actions and low toxicity thereof, is indicated for the treatment of diseases involving disorders of the electrolyte and water balance such as, for example, preterminal and terminal renal insufficiency, malfunctions of the renin-angiotensin-aldosteron system, disorders of the vasopressin secretion, at liquid sequestration ("Third Space" problems such as ascites, glaucoma, brain edema, hydrothorax) as well as other diseases involving an increased extravasal volume accumulation such as lymph edema, EPH gestosis, vena cava stenosis, diseases involving hypoproteinemia such as renal diseases, enteropathioes and liver diseases.

The medicament according to the invention, due to its vasodilative properties, may be used for the treatment of all diseases which are accompanied by an increased vasoconstriction. Thus, the medicament containing urodilatin (ANF/CDD 95-126) according to the invention may be used for the treatment of spasms of vessels such as, for example, Morbus Raynaud, spasms of the muscular distributor arteriae and hearing impairment. Urodilatin (ANF/CDD 95-126) may also be employed for treating further vascular diseases such as, for example, for the treatment of coronary heart disease, *Angina abdominalis*, vasomotor headache, *Arteria basilaris* migraine with blood circulation disorders in the vertebralis-basilaris flow path region and Bing-Horton syndrome.

The medicament containing urodilatin (ANF/CDD 95-126) according to the invention, due to its blood pressure-lowering properties which become effective above all with primarily increased blood pressure, is indicated for malignant hypertonia, hypertonia of pregnancy, headache upon hypertonia, hypertonia in combination with other diseases, for example gout and diabetes.

The medicament according to the invention exhibits antagonistic properties against sodium-retaining, water-retaining and vasoconstrictive hormones. This enables the use of the medicament according to the invention for the treatment of primary and secondary hyperaldosteronism, renovascular hypertony, renin-secernant tumors, pheochromocytoma, Bartter's syndrome and Schwartz-Bartter's syndrome.

The medicament containing urodilatin (ANF/CDD 95-126) according to the invention can further be used for the treatment of heart insufficiency, in heart transplantations and with artificial hearts, for support in "PEEP" (positive end expiratory pressure), during by-pass operations and with open heart surgery. In respiration with positive and expiratory pressure expiration is effected against superatmospheric pressure.

The medicament according to the invention can be used for prophylaxis of acute renal failure after kidney transplantations, postoperatively and for improving the function of transplanted kidneys by pretreating the transplanted kidneys with the medicament of the invention.

The medicament containing urodilatin (ANF/CDD 95-126) according to the invention can also be used for diagnostic purposes. Since the vasodilation is endothel-independent, a comparison with an endothel-dependent vasodilator allows to make a statement on the condition of the endothel.

The use of the medicament according to the invention is also indicated at gastro-intestinal indications such as changes in the pancreas secretion and concomitant utilization disorders, nutritional defects, exocrine pancreas insufficiency, regulations of bowels and bladder (miction and defecation disorders).

In dermatology, the medicament according to the invention may be used for combatting anhidrosis. Also in psychiatry the agent according to the invention may be used for the treatment of cardiovascular side-effects in the therapy of psych(iatr)ic diseases and agitation with catechol release.

These effects are observed already at concentrations within the nanomolar range. However, due to the low toxicity and good compatibility of the agent, higher concentrations may be injected or infused as well.

Urodilatin (ANF/CDD 95-126), in the highly pure form as obtainable by solid phase synthesis, may be used for the preparation of medicaments such as solutions for injection or infusion, nasal spray, ophthalmic drops or as a slow-release form in the case of indications as mentioned above.

The examination of acute toxicity to animals has shown that in a dose range up to 400 µg/kg of body weight no toxic reactions do occur which are detectable using conventional control parameters (biochemistry). An $LD_{50}$ value is not determinable because of the low toxicity of the substance. No serious side-effects were observed in the heart-circulation system, bronchial system, liver and kidney function, gonads and central nervous system.

The pharmacological efficiency of a treatment of the above mentioned diseases ensues from the observed sodiuretic effect which upon intravenous administration results in a rapid increase in diuresis and sodium excretion. Furthermore it has been observed that urodilatin (ANF/CDD 95–126) is capable of compensating the vasoconstrictive effect of noradrenalin.

It has further been observed that the substance inhibits the contracting effect of angiotensin. Of particular interest are cases of serious heart insufficiency with generalized edematosis which do not respond to a conventional therapy. Of considerable importance is also the action on the blood pressure-controlling systems and the vasopressin-controlling systems, so that functional disorders of the posterior lobe of the pituitary gland and psychotropic effects caused thereby are indicated. It is not to be excluded that a more intensive clinical investigation of this substance will result in that further interesting indications are found.

BRIEF DESCRIPTION OF THE FIGURES

The invention is further illustrated by the following FIGURES and EXAMPLES.

Rf Value: 25 minutes
Conditions:
Column: TSK-ODS-120T, 250 mm×4.8 mm
Mobile Solvent A: 40% methanol in water (0.1% of trifluoroacetic acid)
Mobile Solvent B: 100% methanol (of 0.1% trifluoroacetic acid)
Gradient: 10 minutes isocratically A, then during addition of B during 30 minutes increasing to 100% of B
Flow Rate: 0.5 ml/min. 20° C.; paper feed 5 mm/min; calculated absorbance 0.08, UV 254 nm.

Figure 2:
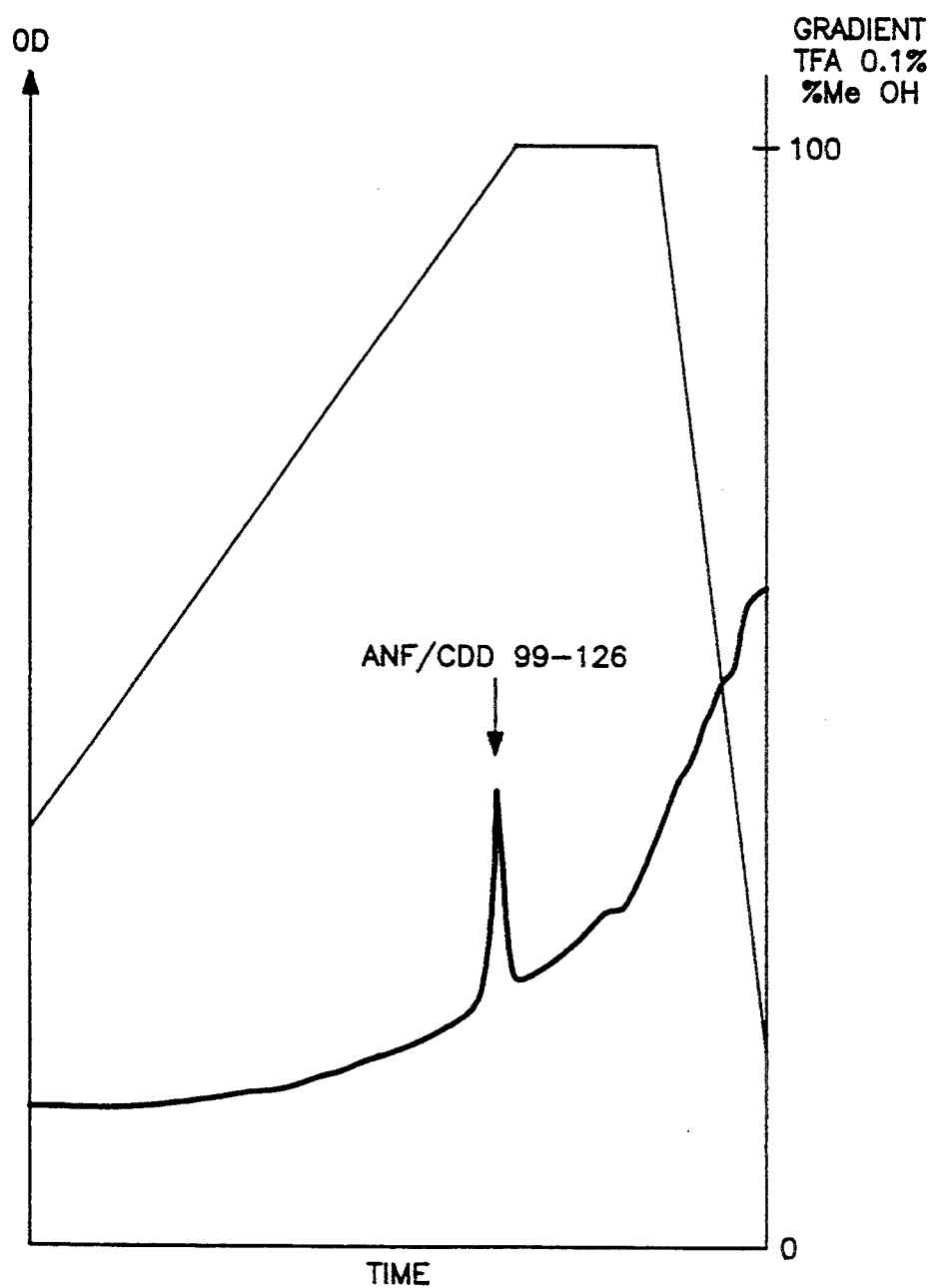

FIG. 2 shows a HPLC chromatogram of ANF/CDD 95–126 using methanol as eluant for comparison.

Figure 1:
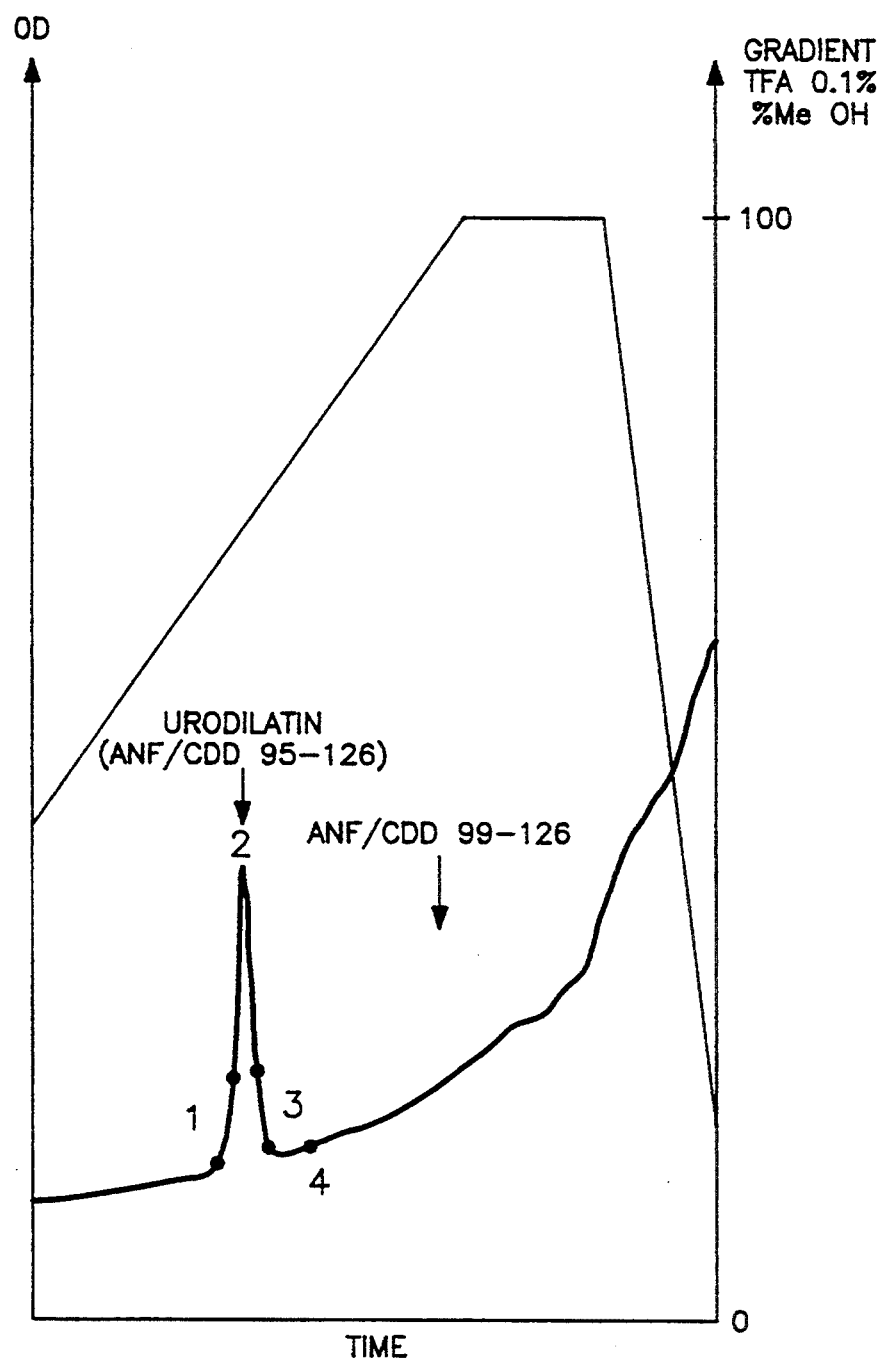
FIG. 1 shows a HPLC chromatogram of urodilatin (ANF/CDD 95–126), isolated from urine. The eluant is methanol.

Rf Value: 35 minutes
The conditions were the same as in FIG. 1.

Figure 3:
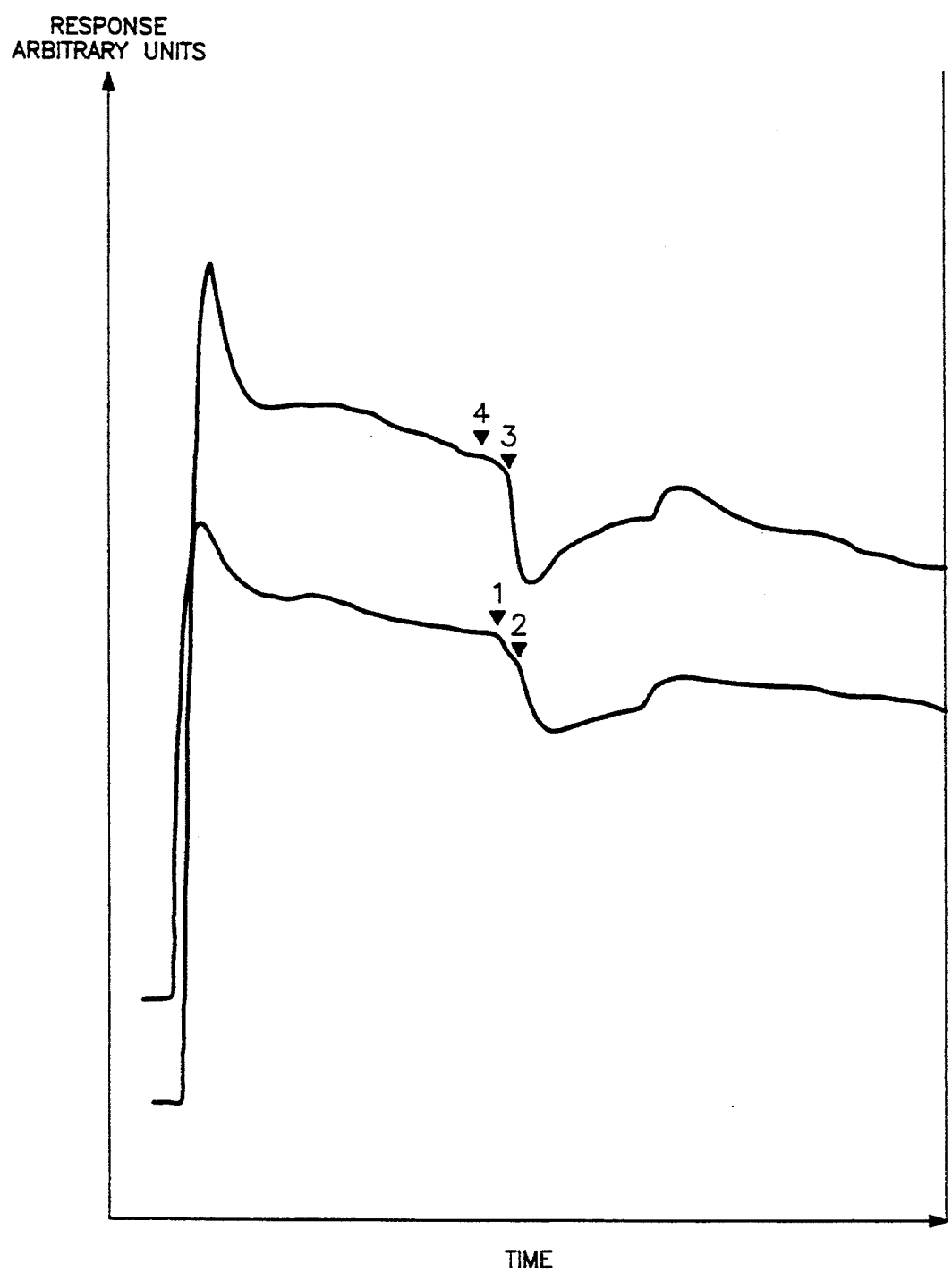

FIG. 3 shows a diagram, wherein biological activity of urodilatin (ANF/CDD 95–126) is demonstrated. Tested were the fractions 1 to 4 of the HPLC as shown in FIG. 1 in the relaxation assay using aorta muscle strips. the doses were 1 μl of each of the HPLC fractions per 10 ml of organ bath {1 μl corresponds to about 3 μg of urodilatin (ANF/CDD 95–126)}.

Figure 4:
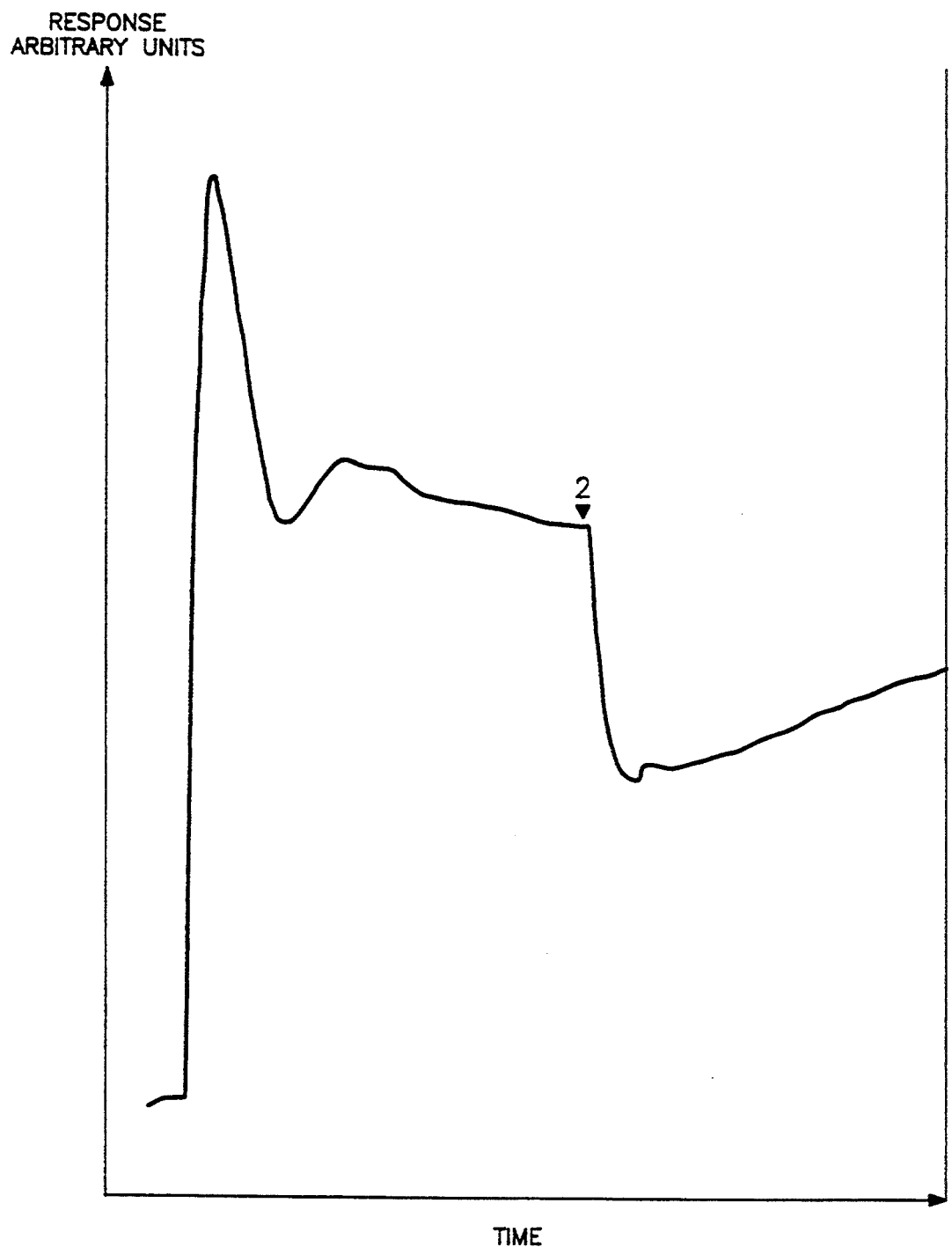

FIG. 4 shows a diagram, wherein the biological activity of the fraction II is demonstrated in the same manner as in FIG. 3.

Figure 5:
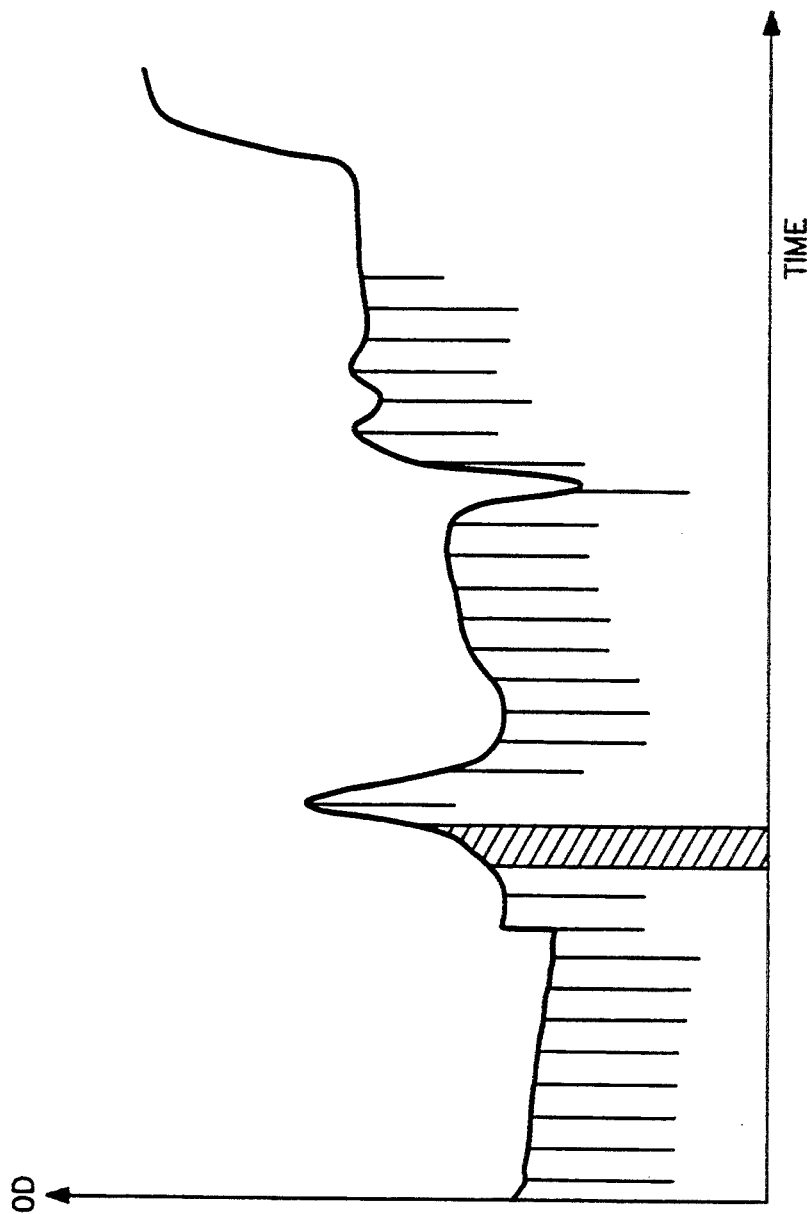

FIG. 5 shows a HPLC diagram. The hatched area represents the main proportion having bioactivity of the cardiodilatin type.

Figure 6:
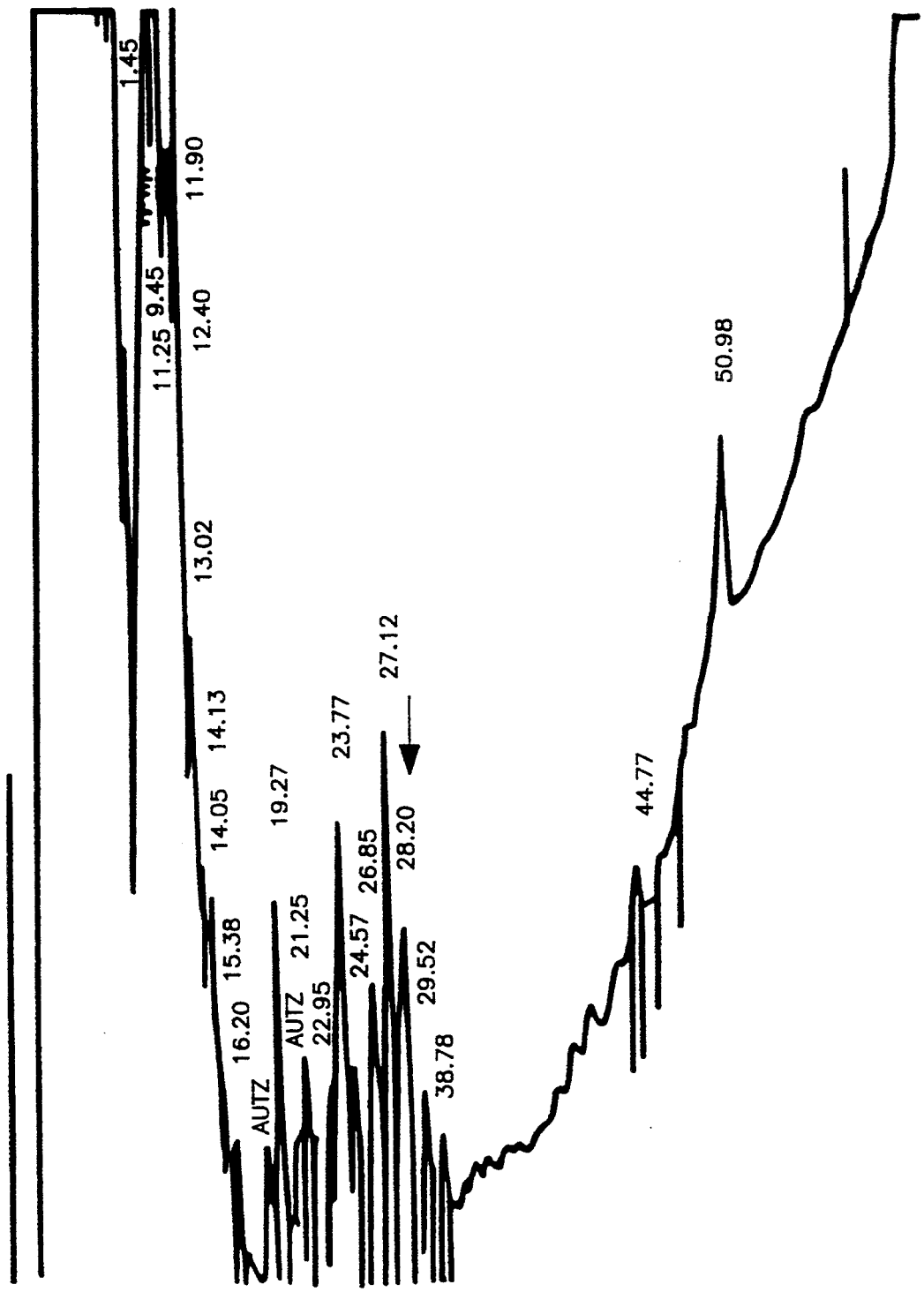

FIG. 6 shows a HPLC diagram comprising 10 individual peaks only one of which, i.e. the peak of a retention time of 28.2 min. (hatched) contains the biologically active substance.

Figure 7:
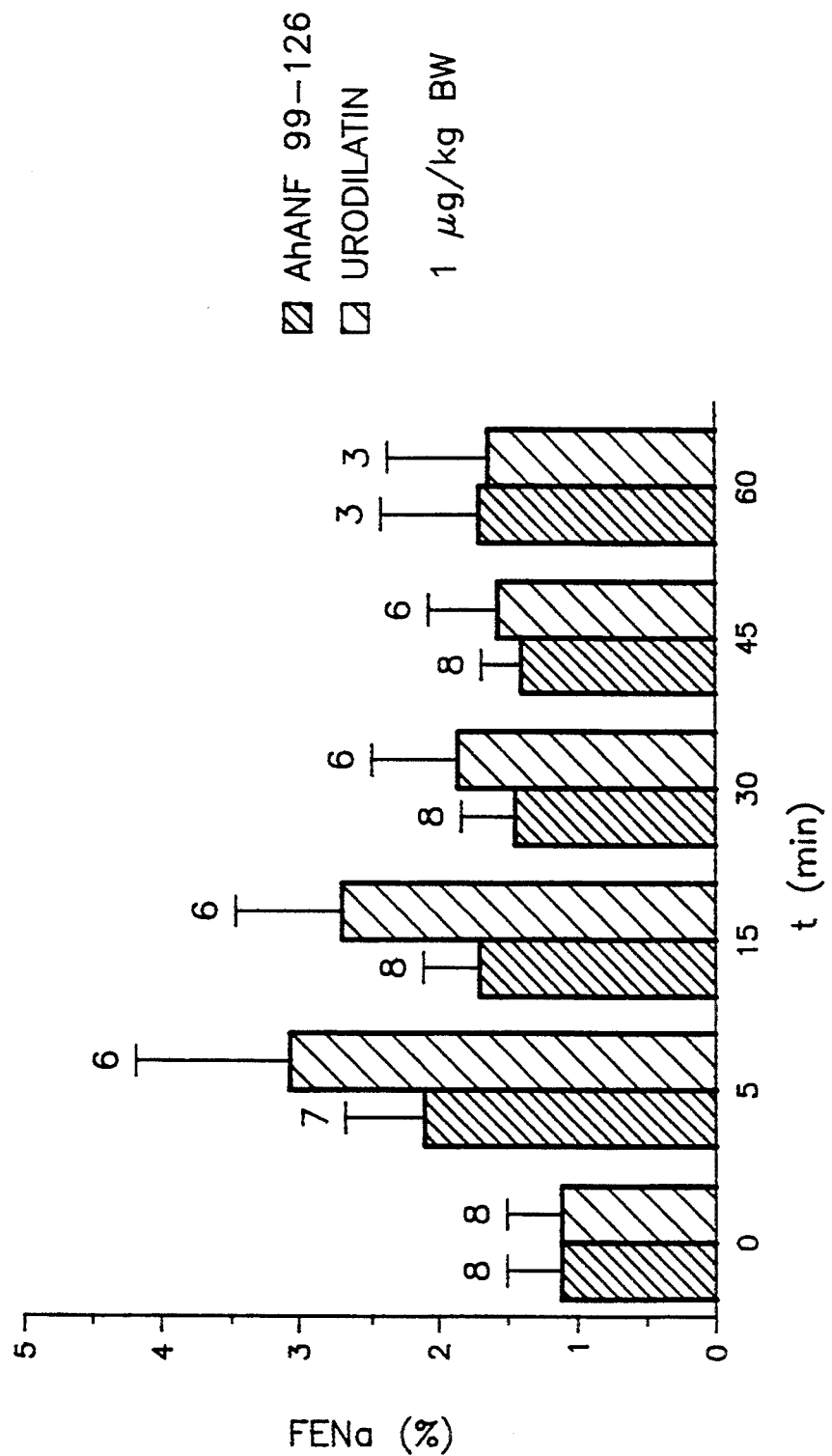

FIG. 7 shows Fractional sodium excretion following bolus injection of 1 μg/kg b.w. hANF or urodilatin.

Figure 8:
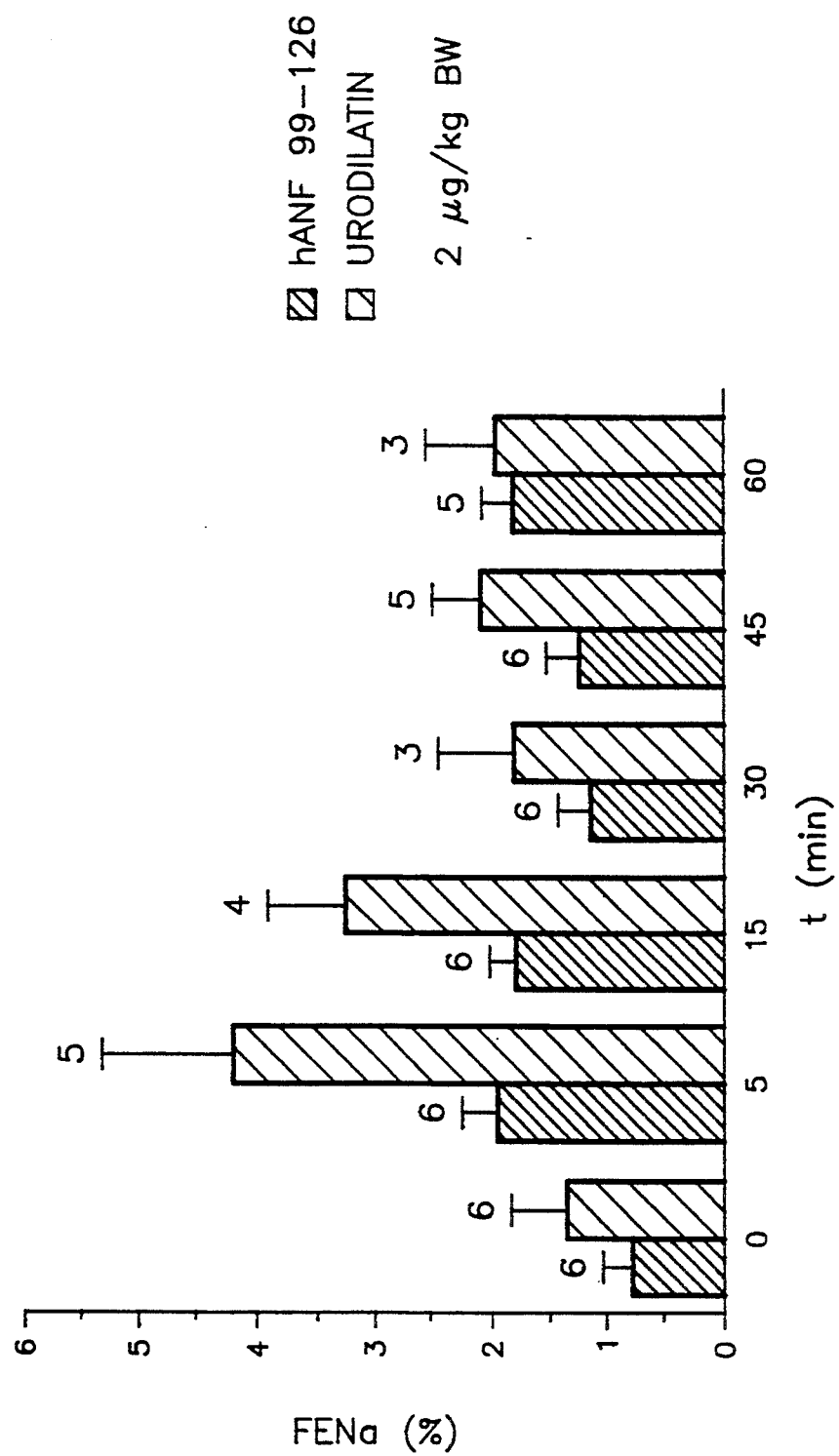

FIG. 8 shows Fractional sodium excretion following bolus injection of 2 μg/kg b.w. hANF or urodilatin.

Figure 9:
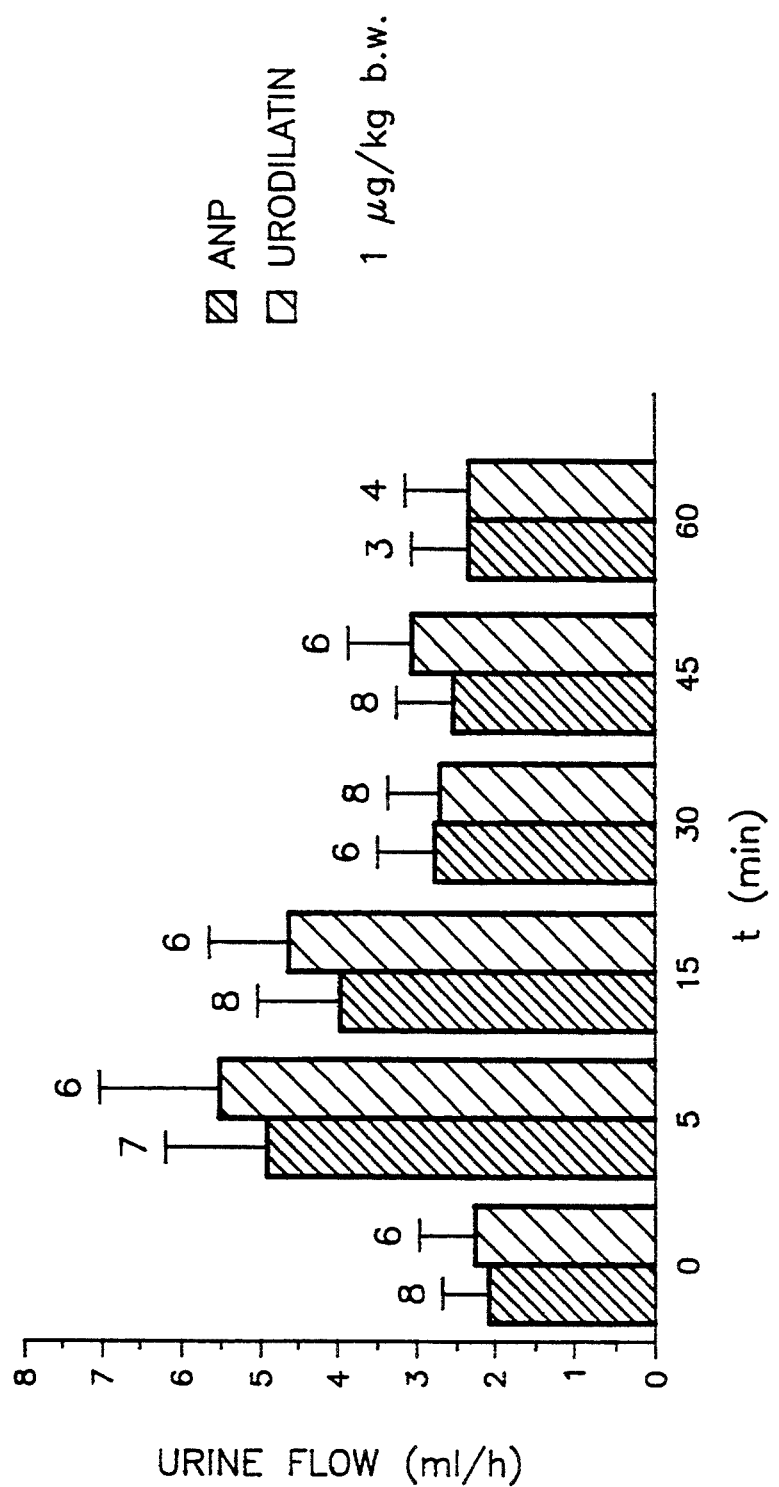

FIG. 9 shows Urine flow following bolus injection of 1 μg/kg b.w. hANF or urodilatin.

Figure 10:
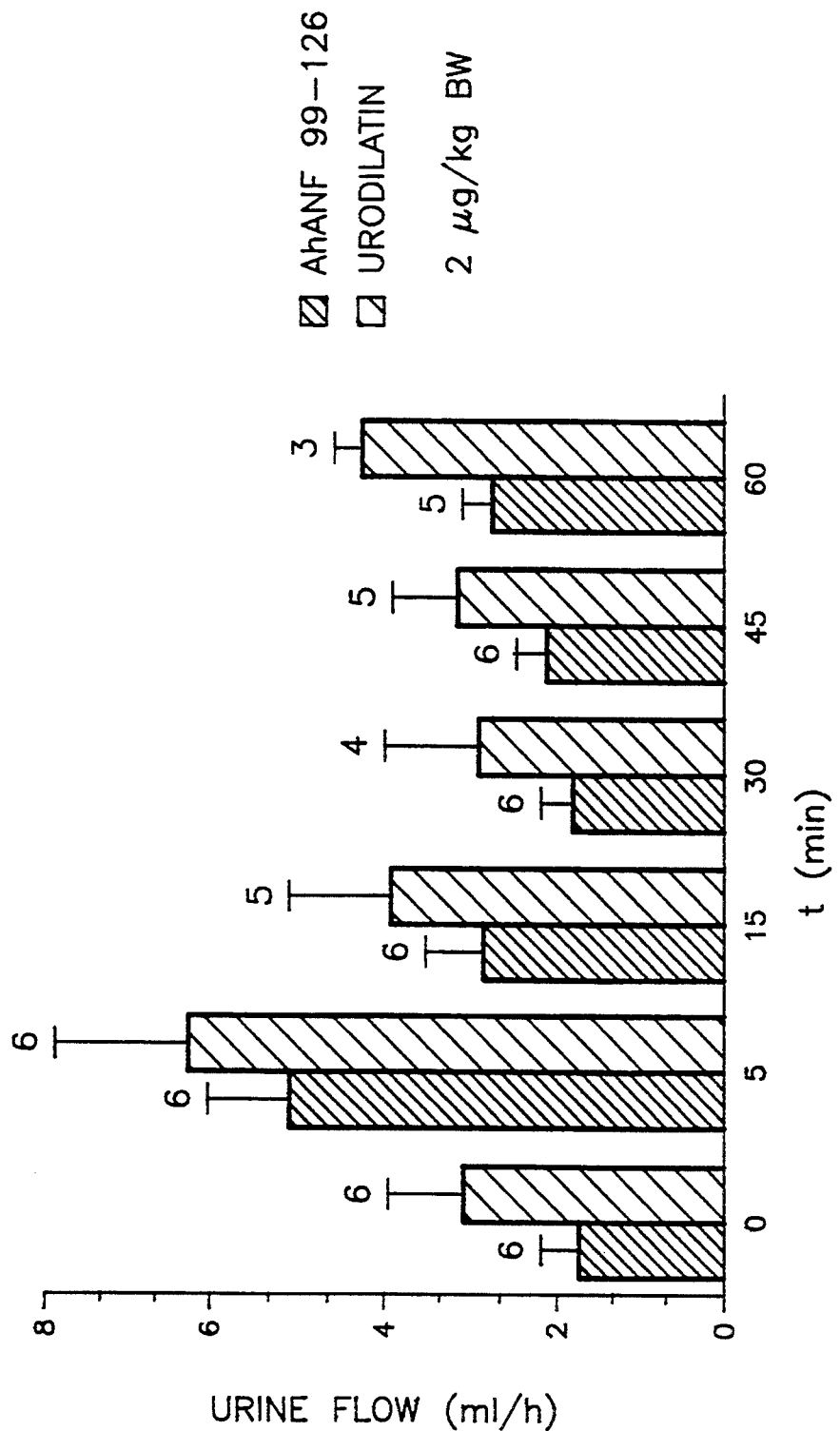

FIG. 10 shows Urine flow following bolus injection of 2 μg/kg b.w. hANF or urodilatin.

Figure 11:
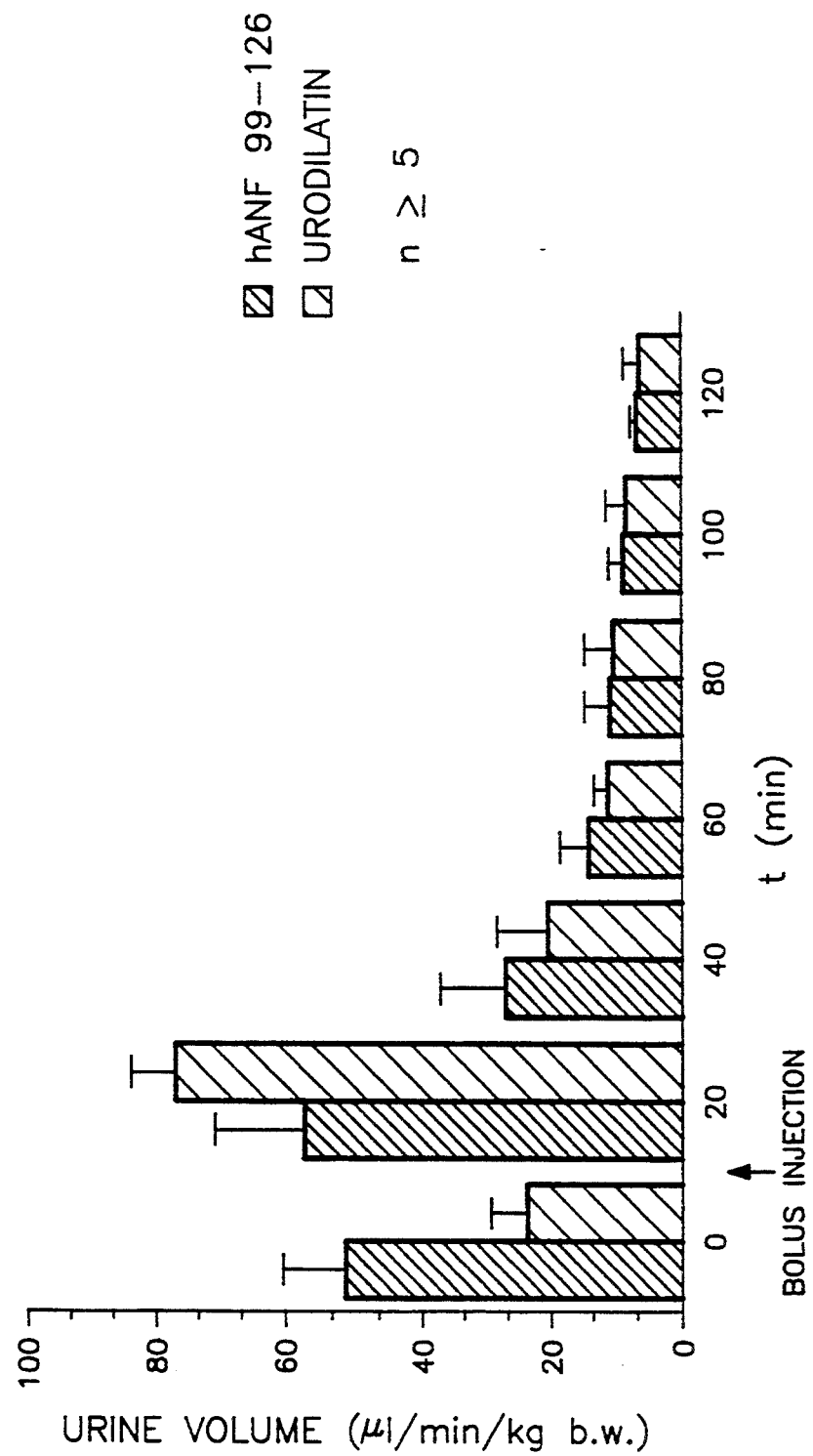

FIG. 11 shows Urine volume following bolus injection of 30 μg hANF or urodilatin.

Figure 12:
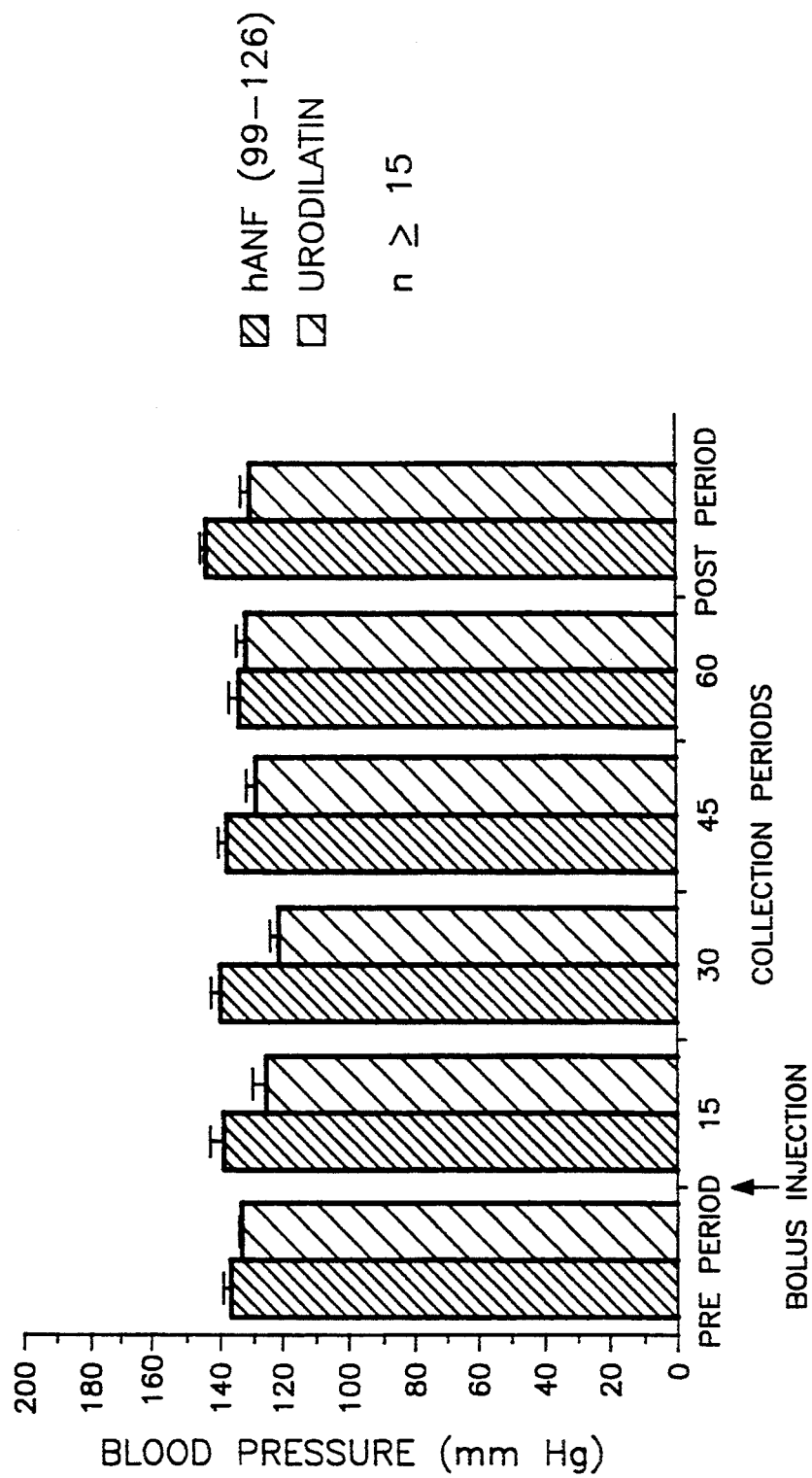

FIG. 12 shows Blood pressure following bolus injection of 30 μg hANF or urodilatin.

EXAMPLE 1

Urine of healthy humans was employed. The urine was immediately acidified with glacial acetic acid to a final concentration of 0.2M. Batches of 200 to 400 l each were diluted with water in a ratio of 1:1 and then adjusted to a pH 2.7 with concentrated hydrochloric acid. Added to the first batch were 2.5 kg of alginic acid, and the mixture was stirred from 8 to 12 hours. then the alginic acid settled, and the supernatant was replaced by a new batch of acidified urine. This procedure was repeated until more than 1,000 l of urine had been reacted with the 2.5 kg of alginic acid. Then the alginic acid was sedimented, separated from the supernatant and washed with ethanol and 0.005M hydrochloric acid on a Büchner funnel. the polypeptides precipitated on the alginic acid were then eluted with 0.2M hydrochloric acid. The pH of the eluate was adjusted to 4.0, and sodium chloride was added to saturation. After 24 hours at 4° C., a salt cake was taken off which had been formed on the salt-saturated solution.

This procedure was monitored by means of a radioimmunoassay for cardiodilatin whereby it showed that more than 90% of the detectable substance had been obtained. then the salt cake was charged onto a Sephadex G-25 column, and the peptides obtained were tested by means of a bioassay for cardiodilatin using aorta muscle stripes. The fraction containing most of the cardiodilatin bioactivity were then lyophilized and chromatographed on an ion exchanger column. The bioactive vasorelaxant material was found in those fractions which were eluted at the highest ionic strength with stepwise gradient.

In the first HPLC there was used a reversed-phase column TSK-ODS-120T. As the eluant there was employed water-acetonitrile-HCl with a continuous gradient. the bioactive materials appear at the same location where synthetic ANF/CDD 99–126 as employed for comparison is eluted. The bioactive fractions were charged onto an analytical reversed-phase column of the same type, while elution was effected using water-methanol-trifluoroacetic acid with a continuous gradient as shown in FIG. 1. Now the bioactive material exhibited a retention time of 25 minutes, whereas synthetic ANF/CDD 99–126 as employed for comparison was eluted after 35 minutes (FIG. 2).

EXAMPLE 2

Structure Elucidation:

The biological material accumulated from human urine according to FIG. 1 and having cardiodilatin-like activity other than ANF/CDD 99–126 (FIG. 2) was subjected to chromatography on a HPLC tandem column (TSK 3000 SW+TSK 2000 SW) in the buffer system 6M guanidine/HCl (50 mM PO$_4$) at pH 6.0 and room temperature. The major proportion of the cardiodilatin-like bioactivity was found in the minor fraction 62 of this purification step (hatched area in FIG. 5). The liquid volume of the fraction 62 was adjusted to 0.1% with trifluoroacetic acid and applied onto a C-18-SEPAK (tradename) cartridge for desalting. To this end the loaded cartridge was subsequently washed with water (0.1% of trifluoroacetic acid) until salt-free. Then the biologically active material was eluted from the cartridge with methanol (or acetonitrile). The eluate was lyophilized. the lyophilizate was again taken up in water (0.1% of trifluoroacetic acid) and separated by means of RP-HPLC.

Column: 125 mm × 4 mm; C-4-phase. ORPEGEN, HD gel.
Buffer A: Water (0.1% of trifluoroacetic acid)
Buffer B: 20% of water in acetonitrile (of 0.1% trifluoroacetic acid)
Flow Rate: 0.5 ml/min;
Temperature: 45° C.
Detection: 230 nm/0.04 Det. Sens.

The HPLC diagram showed more than ten individual peaks in the separation field (FIG. 6), only one of which (marked by an arrow) at a retention time of 28.2 minutes contains the biologically active substance. This peak has been designated as Peak No. 8. Sequence Analysis:

A stepwise Edmann degradation of the intact peptide (Peak No. 8, retention time 28.2 minutes in FIG. 6) was carried out in a gas phase-protein-sequencer 420 A of the company Applied Biosystems. the PTH amino acids were identified by high performance liquid chromatography according to Lottspeich ("High Performance Liquid Chromatography in Protein and Peptide Chemistry", pages 259–268, Lottspeich F., Henschen A., Hupe K. P.; Walter de Gryter, Berlin/New York 1981). The highly purified polypeptide had the following amino acid sequence:

Thr—Ala—Pro—Arg—Ser—Leu—Arg—Arg—Ser—Ser—Cys—Phe—Gly—Gly—Arg—Met—Asp—Arg—Ile—Gly—Ala—Gln—Ser—Gly—Leu—Gly—Cys—Asn—Ser—Phe—Arg—Tyr—OH.

Amino Acid Analysis:

The highly purified polypeptide (Peak No. 8, retention time 28.2 minutes in FIG. 6) was hydrolyzed in 6M HCl, 1.0% of phenol at 110° C. in evacuated tubes for 24 hours. The total composition was determined in Waters-Amino Acid-Analysis System after derivatization with phenylisothiocyanate. The analysis showed a high degree of conformity between the primary structure as obtained by sequence analysis and the total composition, and more specifically so for the values of Tyr 0.9 (1); Met 0.99 (1); Cys 2.1 (2); Ile 1.1 (1); Leu 2.1 (2); Arg 6.4 (6).

EXAMPLE 3

Stepwise Synthesis on a Solid PHase (ABI-Synthesizer 430)

Starting with 1.22 g of Boc-Tyr (Bzl) -Merrifield support (0.67 mMol/g; 1% of DVB; 200–400 mesh) the sequence is synthesized according to the ABI Standard program according to the Boc strategy. Double couplings are carried out up to Ile (113), and triple couplings are carried out from Arg (112). The following Boc amino acids are employed:

Boc—Gly, Boc—Ala, Boc—Leu, Boc—Ile, Boc—Phe,
Boc—Met, Boc—Pro, Boc—Asn, Boc—Gln, Boc—Asp (OBzl),
Boc—Ser (Bzl), Boc—Thr (Bzl), Boc—Cys (Acm),
Boc—Arg (Tos).

The dried peptide-polystyrene is treated with HF with the addition of 5% of anisol and 2.5% of ethylmethylsulfide at 0° C. for 1 hour. Upon removal of the HF in vacuo the crude peptide is washed with AcOH from the polymeric support, and the filtrates are lyophilized. Then the crude lyophilizate is desalted on Sephadex LH 20/water (1% AcOH/1% TFEtOH).

For Acm-removal and cyclization a 5 mM solution of the peptide AcOH/H₂O (9:1; v:v) is prepared, and 1.5 eq. of HCl is added thereto. A concentrated solution of 10 eq. of iodine in AcOH are added at once with vigorous stirring to the peptide solution. After 15 minutes the reaction is terminated by the addition of a diluted ascorbic acid solution in 0.5M citric acid. After lyophilization the material is desalted over Sephadex LH 20/water (1% AcOH/1% TFEtOH) and purified after re-chromatography on Fractogel TSK-HW 40/water (10% AcOH/1% TFEtOH) by means of preparative HPLC.

EXAMPLE 4

Synthesis by Fragment Condensation on a Polymeric Support

On the analogy of Example 1 the sequence is built up to Ser (99). After Boc-removal and deprotonation of 0.5 g of peptide (99–126) -polystyrene coupling is affected in 5 ml of dichloromethane in a shaker reactor at 20° C. for 72 hours by means of 1.609 g (2.1775 mMol; 5-fold excess) of Boc-Thr(But)-Ala-Pro-Arg(Tos) which had been pre-activated with 0.353 g (2.1775 mMol) of 1,1'-carbonyldiimidazole/0.667 g (4.36 mMol) of 1-hydroxybenzotriazole in 5 ml of dichlormethane for 30 minutes. The detachment from the support, Acm-removal, cyclization and work-up and purification are carried out on the analogy of Example 1.

EXAMPLE 5

Synthesis in Solution by Fragment Condensation 2.01 mg (2.72 μMol) of boc-Thr(But)-Ala-Pro-Arg(Tos) are preactivated with 0.44 mg (2.72 μMol) of 1,1'-carbonyl-diimidazol/0.83 mg (5.44 μMol) of 1-hydroxybenzotriazole in 2 ml of DMF for 30 minutes and added to a solution of 5 mg (1.36 μMol; peptide content: 84%) of ANF/CDD 99–126 and 0.15 μl (1.36 μMol) of N-Methyl-morpholine in 3 ml of DMF. After stirring at 20° C. for 72 hours the mixture is concentrated in vacuo, admixed with a small amount of a NaHCO₃ solution, then diluted with a small amount of 1% AcOH/1% TFEtOH and chromatographed on LH 20 in 1% AcOH/1% TFEtOH. After treatment with HF/5% anisol/2.5% ethylmethylsulfide the material is subjected to chromatography on LH 20/water (1% AcOH/1% TFEtOH) and then on Fractogel TSK-HW 40 (S)/water (10% AcOH/1% TFEtOH) and finally purified by means of preparative HPLC.

We claim:
1. A peptide having the amino acid sequence 95–126 of ANF/CDD 1–126 (gamma-hANaP) having the designation urodilatin (ANF/CDD 95–126) according to the formula

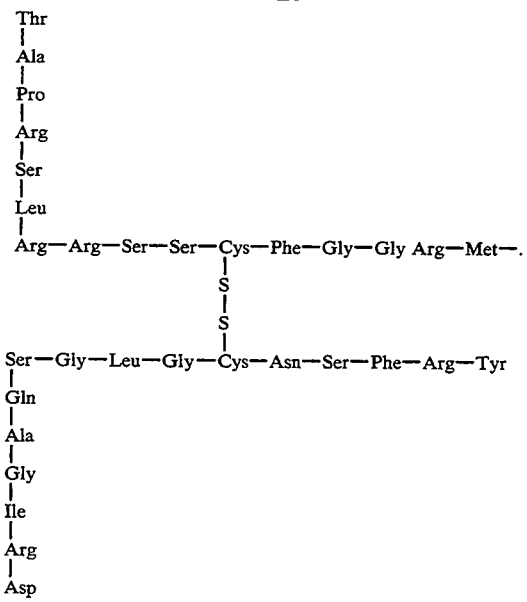

2. Medicament, containing urodilatin (ANF/CDD 95-126) according to claim 1 as the active ingredient in combination with a pharmacologically compatible carrier and/or diluent.

3. The medicament according to claim 2, characterized in that it contains from 10 ng to 50 μg of urodilatin (ANF/CDD 95-126) per dosage unit.

4. A method of treatment of dysfunction relating to blood pressure diuresis, electrolyte and water balance, comprising administration to a subject in need thereof of an amount of urodilatin effective for treatment of the dysfunction.

* * * * *